United States Patent
Kyusojin et al.

(10) Patent No.: US 10,908,795 B2
(45) Date of Patent: *Feb. 2, 2021

(54) INFORMATION PROCESSING APPARATUS, INFORMATION PROCESSING METHOD

(71) Applicant: Sony Corporation, Tokyo (JP)

(72) Inventors: Hiroshi Kyusojin, Tokyo (JP); Kenji Yamane, Kanagawa (JP); Hirofumi Watanabe, Kanagawa (JP); Naoki Tagami, Tokyo (JP)

(73) Assignee: Sony Corporation, Tokyo (JP)

( * ) Notice: Subject to any disclaimer, the term of this patent is extended or adjusted under 35 U.S.C. 154(b) by 68 days.

This patent is subject to a terminal disclaimer.

(21) Appl. No.: 16/246,877

(22) Filed: Jan. 14, 2019

(65) Prior Publication Data

US 2019/0146663 A1 May 16, 2019

Related U.S. Application Data

(63) Continuation of application No. 14/420,981, filed as application No. PCT/JP2013/004906 on Aug. 20, 2013, now Pat. No. 10,235,029.

(30) Foreign Application Priority Data

Aug. 28, 2012 (JP) .................................. 2012-187659

(51) Int. Cl.
*G06F 3/0484* (2013.01)
*G16H 40/63* (2018.01)
(Continued)

(52) U.S. Cl.
CPC ........ *G06F 3/04845* (2013.01); *G06F 3/0482* (2013.01); *G06F 3/04842* (2013.01);
(Continued)

(58) Field of Classification Search
CPC .. G06F 19/321; G06F 3/04845; G06F 3/0482; G06F 3/04842; G06K 9/00134; G16H 30/20; G16H 40/63; G16H 19/321
See application file for complete search history.

(56) References Cited

U.S. PATENT DOCUMENTS

| 7,194,118 B1 | 3/2007 | Harris et al. |
| 2007/0097109 A1 | 5/2007 | Shoemaker et al. |

(Continued)

FOREIGN PATENT DOCUMENTS

| CN | 101989173 | 3/2011 |
| CN | 102467919 | 5/2012 |

(Continued)

OTHER PUBLICATIONS

Office Action issued in JP application 2012187659, dated Dec. 22, 2015 (4 pages).

(Continued)

*Primary Examiner* — Haoshian Shih
(74) *Attorney, Agent, or Firm* — K&L Gates LLP

(57) ABSTRACT

An information processing apparatus is provided comprising a processor; and a memory device storing instructions. When executed by the processor, the instructions cause the processor to generate scene information to reproduce display of at least one selected area of a pathological image; and receive order information corresponding to the scene information based on a user input. In another embodiment, the instructions cause the processor to receive scene information to display at least one selected area of a pathological image and order information corresponding to an order of the scene information; and control display of the at least one selected area of the pathological image in the order based on the scene information and the order information.

20 Claims, 15 Drawing Sheets

(51) Int. Cl.
    *G06F 19/00*     (2018.01)
    *G06F 3/0482*     (2013.01)
    *G16H 30/20*     (2018.01)

(52) U.S. Cl.
    CPC ........... *G06F 19/321* (2013.01); *G16H 30/20* (2018.01); *G16H 40/63* (2018.01)

(56) References Cited

U.S. PATENT DOCUMENTS

| | | | |
|---|---|---|---|
| 2008/0147317 A1* | 6/2008 | Ohn | G01C 21/265 701/532 |
| 2009/0185053 A1 | 7/2009 | Ejima et al. | |
| 2009/0208076 A1 | 8/2009 | Nakajima | |
| 2010/0054556 A1 | 3/2010 | Novatzky et al. | |
| 2011/0026901 A1 | 2/2011 | Kashima | |
| 2011/0060766 A1 | 3/2011 | Ehlke et al. | |
| 2011/0129135 A1 | 6/2011 | Mizutani et al. | |
| 2012/0011568 A1 | 1/2012 | Tahan | |

FOREIGN PATENT DOCUMENTS

| | | |
|---|---|---|
| JP | 10-133946 | 5/1998 |
| JP | 2002-314918 | 10/2002 |
| JP | 2005-176216 | 6/2005 |
| JP | 2006-343573 | 12/2006 |
| JP | 2007-221681 | 8/2007 |
| JP | 2011-064602 | 3/2011 |
| JP | 2011-082915 | 4/2011 |
| JP | 2011-244494 | 12/2011 |
| WO | 2007/069471 | 6/2007 |

OTHER PUBLICATIONS

Chinese Office Action (with English translation) dated Nov. 29, 2018 in corresponding Chinese application No. 201380044184.5 (17 pages).

Chinese Office Action (with English translation) dated Nov. 6, 2017 in corresponding Chinese application No. 201380044184.5 (32 pages).

Article 94(3) Communication dated Nov. 9, 2017 for European Application No. 13 759 323.2 (5 pages).

Microsoft powerpoint2010 reference, 2010, "Powerpoint2010.pdf" 11 pages.

Chinese Office Action (with English translation) dated Oct. 8, 2016 in corresponding Chinese application No. 201380044184.5 (20 pages).

Japanese Office Action dated May 31, 2016 in corresponding Japanese application No. 2012-187659 (4 pages).

International Search Report issued in connection with International Patent Application No. PCT/JP2013/004906 dated Oct. 25, 2013 (4 pages).

* cited by examiner

| Scene number | Slide name | X | Y | Z | Magnification | Rotation angle | Color adjustment |
|---|---|---|---|---|---|---|---|
| 1 | Slide A | 1024 | 845 | 1 | 20 | 0 | No |
| 2 | Slide A | 3624 | 1354 | 2 | 10 | 0 | No |
| 3 | Slide B | 2324 | 2540 | 1 | 20 | 90 | sharpness=1.0 |
| 4 | Slide B | 1024 | 845 | 1 | 20 | 0 | No |

FIG.8

| Presentation order | Scene number |
|---|---|
| 1 | 3 |
| 2 | 4 |
| 3 | 1 |
| 4 | 2 |

| Presentation order | Scene number | Moving method |
|---|---|---|
| 1 | 3 | Animation |
| 2 | 4 | Animation |
| 3 | 1 | Jump |
| 4 | 2 | Zoom-out-and-zoom-in |

| Presentation order | Scene number | Moving method | Display time period (second) |
|---|---|---|---|
| 1 | 3 | Animation | 60 |
| 2 | 4 | Animation | 120 |
| 3 | 1 | Jump | 60 |
| 4 | 2 | Zoom-out-and-zoom-in | 200 |

| Presentation order | Scene number /action |
|---|---|
| 1 | 3 |
| 2 | 4 |
| 3 | Display annotations "a" and "b" |
| 4 | 1 |
| 5 | 2 |

INFORMATION PROCESSING APPARATUS, INFORMATION PROCESSING METHOD

CROSS REFERENCES TO RELATED APPLICATIONS

The present application is a continuation of U.S. application Ser. No. 14/420,981, filed on Feb. 11, 2015, which is a 371 International Application of PCT/JP2013/004906, filed on Aug. 20, 2013, which claims priority to Japanese Priority Patent Application JP 2012-187659, filed in the Japan Patent Office on Aug. 28, 2012, the entire content of each of which is hereby incorporated by reference herein.

BACKGROUND

The present disclosure relates to an information processing apparatus capable of making a presentation by using a digital pathological image. The present disclosure further relates to an information processing method.

Recently, "digitalization of pathological data" is being developed. According to "digitalization of pathological data", not an optical microscope but a digital pathological scanner takes a picture of a pathological slide. Digitalized pathological data is delivered via a server-client digital pathological system. A digital pathological server stores a digital pathological image, which is taken by a digital pathological scanner. The stored digital pathological image is delivered to a digital pathological viewer. Data of the digital pathological image is confirmed and diagnosis is made by using a display.

A digital pathological image is being used at a presentation such as an academic conference or a lecture.

There are proposed many methods for effectively making a presentation by using not a digital pathological image but a small digital image having a general size. For example, according to a technology disclosed in Patent Literature 1, a series of images is selected from images, which are taken by a digital camera. A slide show is created while "adding a title, changing a layout, and the like". Further, Patent Literature 2 proposes the following system. A series of selected images is analyzed. An "automatic slide show" is displayed based on a display time period for each image.

CITATION LIST

Patent Literature

PTL 1: Japanese Patent Application Laid-open No. 2005-176216
PTL 2: Japanese Patent Application Laid-open No. 2011-244494

SUMMARY

Technical Problem

The number of pixels of a digital pathological image is more than 1,000 times the number of pixels of a digital image taken by a single-lens reflex camera. Because the digital pathological image has such a huge file size, it takes time to enlarge and display a desired position. Further, because of difficulty of pathology itself, it also takes time to find out a position in a sample, which exhibits a particular symptom. Meanwhile, if a state where a desired position is displayed is stored as a still image, the problem of the huge number of pixels may be avoided. However, operation of zooming in/out a displayed image while keeping an image quality and an image size may not be performed, different from a digital pathological viewer. In view of this, it is desirable to provide a scheme of making a presentation efficiently by using a digital pathological viewer.

In view of the above-mentioned circumstances, it is desirable to provide an information processing apparatus, an information processing method, each of which is capable of making a presentation efficiently by using a digital pathological image.

Solution to Problem

In an embodiment, an information processing apparatus is provided that comprises a processor; and a memory device storing instructions which when executed by the processor, causes the processor to generate scene information to reproduce display of at least one selected area of a pathological image; and receive order information corresponding to the scene information based on a user input.

In an embodiment of the information processing apparatus, the scene information includes position information, magnification information, and rotation angle information.

In an embodiment of the information processing apparatus, the instructions further cause the processor to generate moving information indicating a method of moving between a first selected area of the pathological image and a second selected area of the pathological image. The method of moving may include at least of one an animation, a jump, a zoom in, and a zoom out.

In an embodiment of the information processing apparatus, the instructions further cause the processor to generate display time information indicating a time period for displaying the at least one selected area of the pathological image.

In an embodiment of the information processing apparatus, the instructions further cause the processor to generate annotation information indicating annotations to be displayed with the at least one selected area of the pathological image.

In an embodiment of the information processing apparatus, the instructions further cause the processor to control display of the at least one selected area of the pathological image. In an embodiment of the information processing apparatus, the scene information includes depth information of the at least one selected area of the pathological image. In an embodiment of the information processing apparatus, the scene information is generated based on an image displayed on a display screen.

In an embodiment, an information processing method is provided comprising generating scene information to reproduce display of at least one selected area of a pathological image; and receiving order information corresponding to the scene information based on a user input.

In an embodiment, a non-transitory computer readable storage medium storing a computer program is provided. The computer program causes an apparatus to generate scene information to reproduce display of at least one selected area of a pathological image; and receive order information corresponding to the scene information based on a user input.

In an embodiment, an information processing system is provided comprising: a processor; and a memory device storing instructions which when executed by the processor, causes the processor to: generate scene information to reproduce display of at least one selected area of a pathological image; and receive order information corresponding to the scene information based on a user input. The information processing system may also comprise at least one of a server configured to store the pathological image and a pathological scanner configured to capture the pathological image.

In an embodiment, an information processing apparatus is provided comprising: a generating unit configured to generate scene information to reproduce display of at least one selected area of a pathological image; and a receiving unit configured to receive order information corresponding to the scene information based on a user input.

In an embodiment, an information processing apparatus is provided comprising: a processor; and a memory device storing instructions which when executed by the processor, causes the processor to: receive scene information to display at least one selected area of a pathological image and order information corresponding to an order of the scene information; and control display of the at least one selected area of the pathological image in the order based on the scene information and the order information.

In an embodiment of the information processing apparatus, the instructions further cause the processor to switch between display and non-display of display elements displayed with the at least one selected area of the pathological image.

In an embodiment of the information processing apparatus, the scene information is received based on an image displayed on a display screen.

In an embodiment, an information processing method is provided comprising: receiving scene information to display at least one selected area of a pathological image and order information corresponding to an order of the scene information; and controlling display of the at least one selected area of the pathological image in the order based on the scene information and the order information.

In an embodiment, a non-transitory computer readable storage medium storing a computer program is provided. The computer program causes an apparatus to: receive scene information to display at least one selected area of a pathological image and order information corresponding to an order of the scene information; and control display of the at least one selected area of the pathological image in the order based on the scene information and the order information.

In an embodiment, an information processing system is provided comprising: a processor; and a memory device storing instructions which when executed by the processor, causes the processor to: receive scene information to display at least one selected area of a pathological image and order information corresponding to an order of the scene information; and control display of the at least one selected area of the pathological image in the order based on the scene information and the order information. The information processing system may include at least one a server configured to store the pathological image and a pathological scanner configured to capture the pathological image.

In an embodiment, an information processing apparatus is provided comprising: a reception unit configured to receive scene information to display at least one selected area of a pathological image and order information corresponding to an order of the scene information; and a display control unit configured to control display of the at least one selected area of the pathological image in the order based on the scene information and the order information.

In an embodiment, an information processing system is provided comprising: at least one processor; and a memory device storing instructions which when executed by the at least one processor, causes the processor to: generate scene information to reproduce display of at least one selected area of a pathological image; receive order information corresponding to the scene information based on a user input; and control display of the at least one selected area of the pathological image in the order based on the scene information and the order information. The information processing system may further include at least one of a server configured to store the pathological image and a pathological scanner configured to capture the pathological image.

Advantageous Effects of Invention

As described above, according to the present technology, presentation may be made effectively by using digital pathological images.

BRIEF DESCRIPTION OF THE DRAWINGS

FIG. 8 is a diagram showing a specific example of a scene table in which scene information is registered.

DETAILED DESCRIPTION

Hereinafter, an embodiment of the present technology will be described with reference to the drawings.

First Embodiment (Usage Environment of Digital Pathological Viewer)

Figure 1:
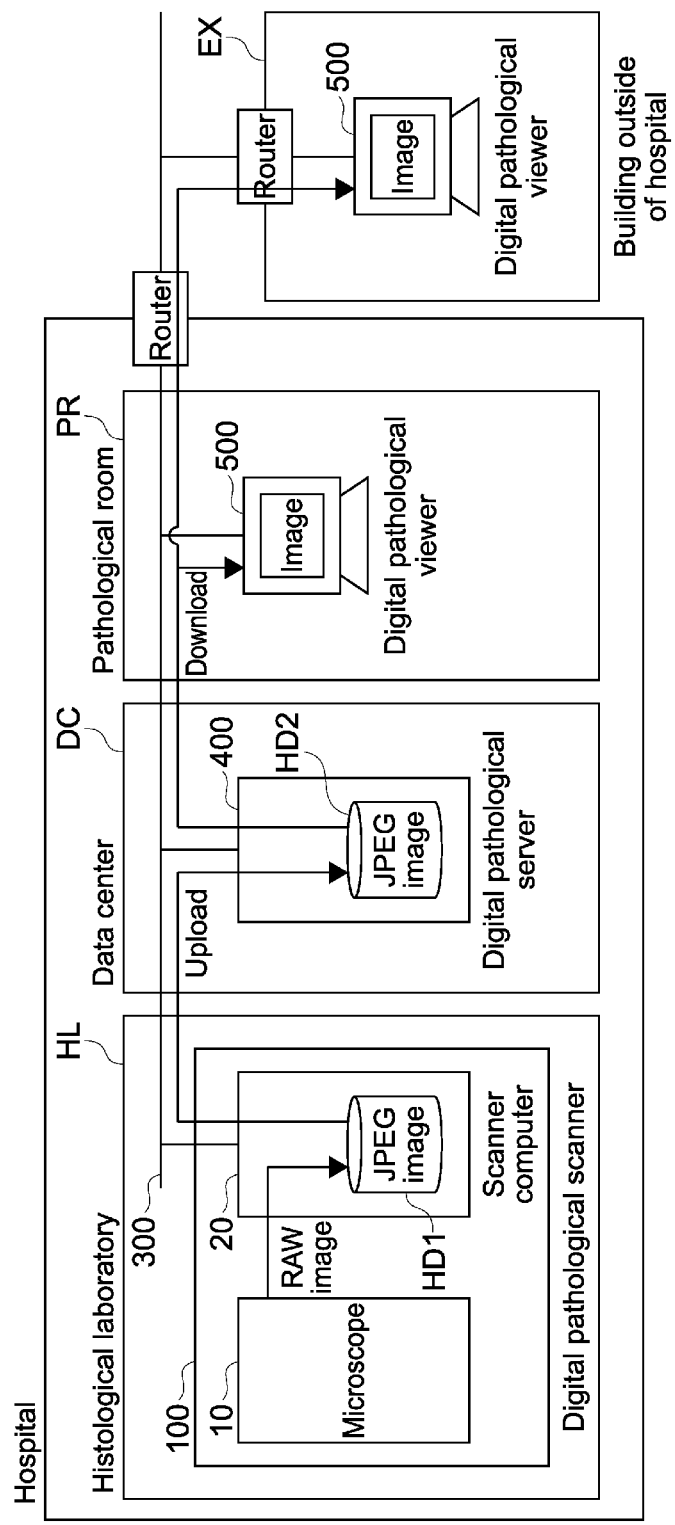
FIG. 1 is a diagram showing a typical usage environment of the digital pathological viewer 500 according to the present technology.

First, the whole picture of an environment of pathology, in which a pathologist makes a diagnosis by using a digital pathological slide (pathological image), will be described. The digital pathological slide (pathological image) is obtained by taking a picture of a specimen by using a microscope. A pathologist uses a digital pathological viewer, observes a digital pathological slide, and makes a diagnosis by using the image. FIG. 1 is a diagram showing a typical usage environment of a digital pathological viewer 500 of the present technology. A presentation using a digital pathological slide is made by using the digital pathological viewer 500.

A digital pathological scanner 100 includes a microscope 10 and a scanner computer 20. The digital pathological scanner 100 is installed in a histological laboratory HL in a hospital. The microscope 10 takes a RAW image. The scanner computer 20 processes the RAW image. Examples of the image processing include processing procedure, shading processing, color balance correction, gamma correction, and 8-bit processing. After that, the processed image is divided into tile images (hereinafter, referred to as tiles). The size of the tiles is, for example 256 pixels×256 pixels. The image divided into tiles is converted into a JPEG (Joint Photographic Experts Group) image, and is compressed. After that, the compressed image is stored in a hard disk HD1.

The hard disk HD1 of the scanner computer 20 stores the JPEG image. Next, the JPEG image is uploaded to a hard disk HD2 via a network 300. The hard disk HD2 is in a digital pathological server 400. The digital pathological server 400 is in a data center DC in the same hospital.

A pathologist as an observer is in a pathological room PR in the hospital or in a building EX outside of the hospital. The pathologist observes a JPEG image stored in the hard disk HD2 of the digital pathological server 400 by using the digital pathological viewer 500. The digital pathological viewer 500 is connected to the digital pathological server 400 via the network 300.

Alternatively, a pathologist as an observer instructs the digital pathological viewer 500 to record an image, which is displayed on a screen of the digital pathological viewer, as a scene (described later).

Further, a pathologist instructs the digital pathological viewer 500 to combine scenes and to make a presentation of digital pathological slides.

(Scene)

Next, a scene will be described. Scene is an image, which a user instructs to store when a digital pathological slide is displayed by using a digital pathological viewer.

Figure 2:
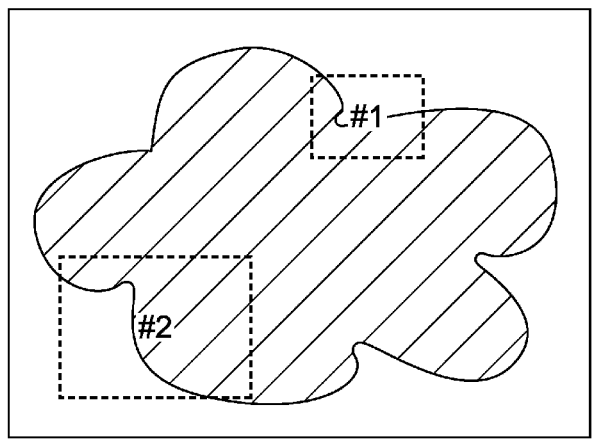
FIG. 2 is a diagram showing a relation between the whole image of a digital pathological slide A, and scenes set in the digital pathological slide A.
Figure 3:
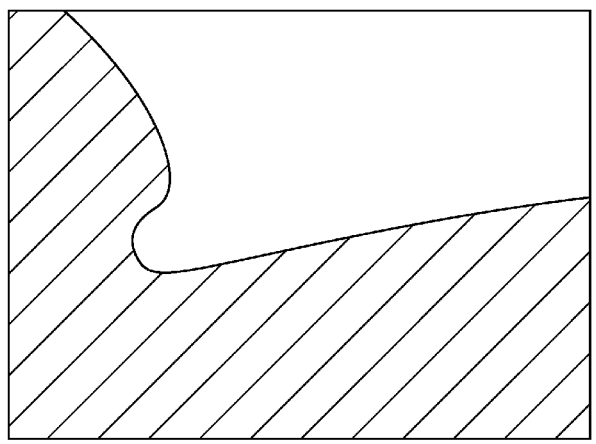
FIG. 3 is a diagram showing an example of a displayed scene of the digital pathological slide.
Figure 4:
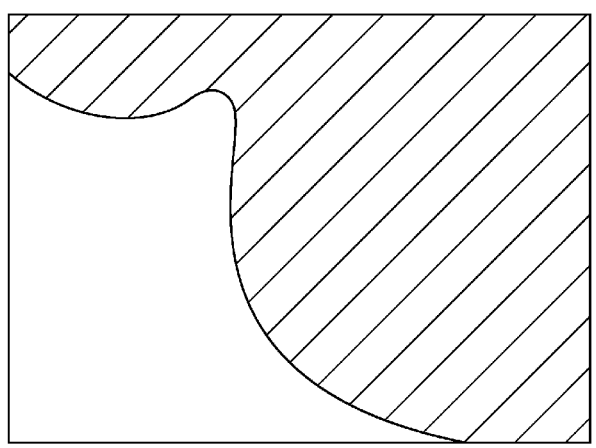
FIG. 4 is a diagram showing an example of a displayed scene of the digital pathological slide.

With reference to FIG. 2 to FIG. 4, the relation between a digital pathological slide and a scene will be described. FIG. 2 is a diagram showing an example of the relation between a whole image of a digital pathological slide A and scenes set in the digital pathological slide A. Each of FIG. 3 and FIG. 4 is a diagram showing an example of a displayed scene in the digital pathological slide. Note that the digital pathological viewer 500 is configured to display an image at an arbitrary coordinate in a digital pathological slide with arbitrary magnification.

For example, a user wishes to show two places in the digital pathological slide A during presentation. The two places are rectangular portions #1 and #2 of FIG. 2. Each of the rectangular portions #1 and #2 is surrounded by a dotted line. First, a user operates the digital pathological viewer 500 such that only the portion #1 is displayed on a screen of the digital pathological viewer 500.

The image of FIG. 3 is displayed on the digital pathological viewer 500. At this time, the user instructs the digital pathological viewer 500 to record the display status of #1 as a scene #1. The user instructs the digital pathological viewer 500 by selecting an option in a pull-down menu on a screen, or by pressing a particular key of a controller (described later).

Next, the user operates the digital pathological viewer 500 such that only the portion #2 is displayed on the screen of the digital pathological viewer 500. The image of FIG. 4 is displayed on the digital pathological viewer 500. At this time, the user instructs the digital pathological viewer 500 to record the display status of #2 as a scene #2. Information on the display status is stored in a scene table (described later) as scene information.

(Scene Table)

Next, a scene table will be described. The scene table includes a scene number, which uniquely identifies each scene, and scene information on each scene.

Note that the scene information is a constituent necessary to reproduce a scene. That is, the scene information is necessary to display the scene on the digital pathological viewer 500 again. The scene information includes the following elements. As described below, the scene information registered in the scene table is not an image but the following numerical values.

(1) Digital pathological slide name (file name)
(2) Coordinates (plane XY coordinate, Z coordinate in focus direction of microscope)
(3) Magnification (twentyfold, fourtyfold, pixel same magnification, digital zoom, etc.)
(4) Rotation angle (left/right 90 degrees, 180 degrees, etc.)
(5) Color adjustment (RGB, gamma, contrast, sharpness, etc.)

Figure 5:
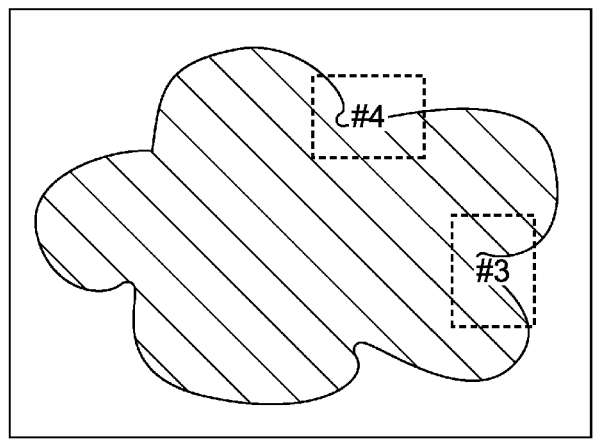
FIG. 5 is a diagram showing relation between the whole image of a digital pathological slide B, and scenes set in the digital pathological slide B.

Here, as an example, let's assume that serial sections are stained with different colors to thereby obtain digital pathological slides A and B, that two scenes are set in the digital pathological slide A, that two scenes are set in the the digital pathological slide B, and that those scenes are used in presentation. FIG. 5 is a diagram showing an example of the relation between a whole image of the digital pathological slide B and scenes set in the digital pathological slide B.

Figure 6:
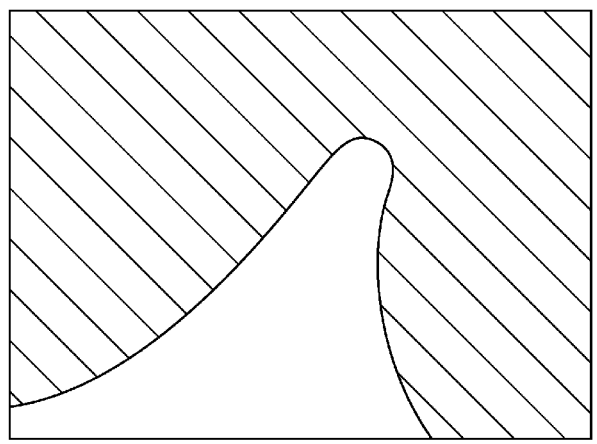
FIG. 6 is a diagram showing an example of a displayed scene of the digital pathological slide.
Figure 7:
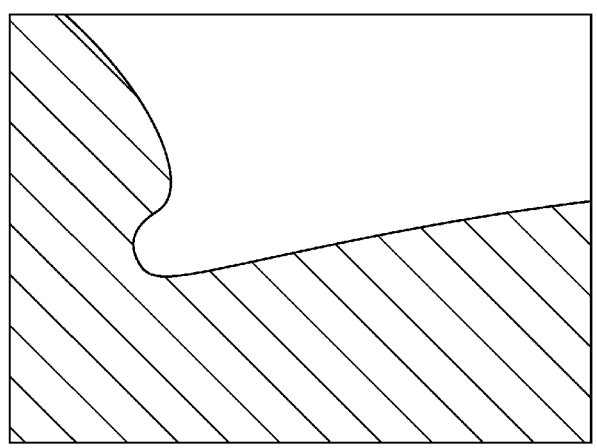
FIG. 7 is a diagram showing an example of a displayed scene of the digital pathological slide.

Each of FIG. 6 and FIG. 7 is a diagram showing an example of a displayed scene in the digital pathological slide.

First, as described above, a user sets the scene #1 in the digital pathological slide A. Then, the user moves the display area while decreasing magnification (enlarging display area), and sets the scene #2. Next, the user changes the displayed slide, and the digital pathological slide B is displayed. Then, as shown in FIG. 5, a rectangular area #3 rotates clockwise by 90 degrees, and the rectangular area #3 is displayed full-screen. Then, the displayed rectangular area #3 is registered as a scene #3. Finally, a rectangular area #4 of FIG. 5 is displayed full-screen as shown in FIG. 7. The rectangular area #4 is registered as a scene #4.

FIG. 8 shows a specific example of a scene table in a case where the scenes #1 to #4 are registered as described above. FIG. 8 is a diagram showing a specific example of a scene table in which scene information is registered. For example, the scene of the scene number 3 (#3) of the scene table indicates a displayed image of FIG. 6. The scene information of this scene shows the following facts. The slide name is the digital pathological slide B. The XY coordinate is (2324, 2540), where the lower left corner of the digital pathological slide is the origin. The Z coordinate is the first slide, where the eye lens side is the origin. The magnification is twentyfold. The displayed image rotates clockwise by 90 degrees. A sharpness filter is applied.

With reference to a scene tray (described later), images of scenes, which are registered in a scene table, are listed.

(Scene Tray)

Next, a scene tray will be described. A scene tray is configured not to list numerical values of the scenes registered in the scene table, but to list images of the scenes. The tray is displayed on the digital pathological viewer 500 in response to a specific instruction from a user.

Figure 9:
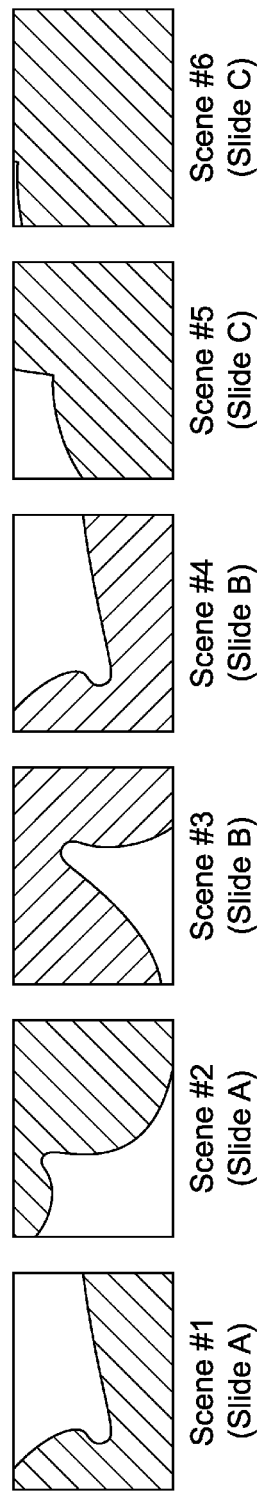
FIG. 9 is a diagram showing an example of a scene tray.

FIG. 9 is a diagram showing an example of the scene tray. In the status of FIG. 9, the scene #1 to a scene #6 are arrayed in the order of registration. A user watches the scene images, and confirms what is registered for each scene. At the same time, the user directly drags and drops the scene images, whereby the order of the scenes is changed. If the order of the scenes is changed, information, which is registered in a scene setting table (described later), is generated.

(Scene Setting Table (Basic Function))

Next, a scene setting table will be described. The most basic function of the scene setting table is to determine the order (order information) of scenes. The scenes are presented to audience when a user makes a presentation by using the digital pathological viewer 500.

Figures 10, 11, 12, 13:
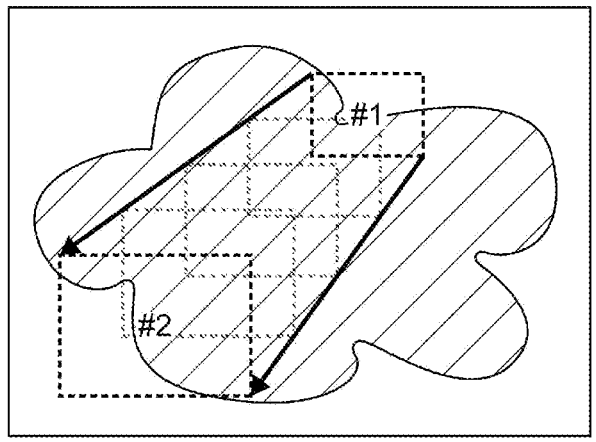
FIG. 10 is a diagram showing an example of a scene setting table.
FIG. 11 is a diagram showing an example of movement between scenes by using animation.
FIG. 12 is a diagram showing an example of a scene setting table, to which a method of moving scenes is additionally specified.
FIG. 13 is a diagram showing an example in which the upper limit of a display time period is additionally set to a scene setting table including moving methods.

FIG. 10 is a diagram showing an example of the scene setting table. In the example of FIG. 10, as premises, the scene #1 to the scene #4 are registered in the scene table. Further, the order of the scenes presented to audience is the scene #3, the scene #4, the scene #1, and the scene #2.

(How a Scene Moves to Another Scene)

Next, how a scene moves to another scene will be described. A user instructs the digital pathological viewer 500 to move from a particular scene to the next scene. In this case, the user clicks the left mouse button, or holds down a particular key of a controller (described later). As a result, the user is capable of instructing the digital pathological viewer 500 easily.

The following is an example of a method of drawing movement of scenes when moving to and from scenes.

(A) Animation

Let's say that a scene is suddenly switched to another scene. In this case, it is difficult for audience other than an operator to understand where in a digital pathological slide they are watching. In view of this, according to this method, when a scene is switched to another scene, the scene moves as follows. A scene moves while animation is displayed such that the coordinate and the magnification of the original scene gradually come close to the coordinate and the magnification of the next scene.

FIG. 11 is a diagram showing an example of how a scene moves to another scene according to the animation method. In FIG. 11, the following situation is shown in the whole image of the digital pathological slide A. The coordinate of the displayed scene #1 of the digital pathological slide A gradually moves, and the display area of the displayed scene #1 is gradually enlarged. Finally, the displayed scene is switched to the scene #2.

(B) Zoom Out and Zoom in

Let's say that movement using the animation is repeated. In this case, it is difficult to understand where the currently-displayed image is at a place in the whole image. In view of this, according to this method, when a scene is switched to another scene, the original scene is once zoomed out at the magnification, with which a user may watch the whole image. Then, the next scene is zoomed in.

For example, the scene #1 of FIG. 3 is displayed. Then, the the scene #1 of FIG. 3 is zoomed out, and the whole image of the digital pathological slide of FIG. 2 is finally displayed. After that, the whole image of the digital pathological slide of FIG. 2 is zoomed in, and the scene #2 of FIG. 4 is finally displayed. Note that, when zooming out a scene, the scene may be zoomed out, and an image may be displayed at the magnification, with which a user may understand the position of the scene in the whole image. That is, it is not always necessary to zoom out a scene until the whole image is displayed.

(C) Jump

Let's say that it is desirable to move a scene to another scene at high speed. Let's say that animation makes no sense because, for example, a digital pathological slide itself is switched. In those cases, a method of suddenly switching a displayed scene to the next scene is effective.

For example, one place of one section, which is stained with a particular color, is compared to the same place of the serial section, which is stained with a different color. In this case, if a scene is switched to another scene by using the jump method, it may be easy to compare one scene to the other scene, and to understand the difference.

(Scene Setting Table (Modified Example 1))

Next, a modified example 1 of the scene setting table will be described. The above-mentioned scene setting table establishes correspondence between the order of presentation of scenes to audience and the scene number. Here, a scene setting table, which additionally specifies a method of moving a scene to another scene, is generated.

The generated scene setting table, which specifies a moving method, is used. In this case, in the case of presentation, a user not only specifies the order of scenes, but also specifies a method of moving a scene to another scene. FIG. 12 is a diagram showing an example of a scene setting table in which a method of moving a scene to another scene is additionally specified. FIG. 12 shows that, for example, in a case where the scene #1 (display order 3) is moved to the scene #2 (display order 4), the zoom-out-and-zoom-in method is used.

(Scene Setting Table (the Modified Example 2))

Next, a modified example 2 of the scene setting table will be described. A scene setting table described in the modified example 2 sets the upper limit of a display time period for each entry of the above-mentioned scene setting table. By setting the upper limit of the display time period, even if a user does not switch a scene to the next scene, the scene is automatically switched to the next scene after a set time period passes.

It is effective to provide the upper limit of the display time period in a case where, for example, the time period for presentation is limited.

FIG. 13 is a diagram showing an example in which the upper limit of a display time period is additionally set to a scene setting table including moving methods. This example shows that, for example, the scene #4 (display order 2) is switched to the next scene #1 after 120 seconds passes, even if an instruction from a user is not received.

(Scene Setting Table (Modified Example 3))

Next, a modified example 3 of the scene setting table will be described. A scene setting table described in the modified example 3 is characterized in that the scene number and in addition annotation names are set for the display order. Note that annotation is a note about diagnosis on a digital pathological slide written by a user.

For example, a user may give audience a question during presentation. The answer may be displayed on the screen of the digital pathological viewer 500.

Figures 14, 15:
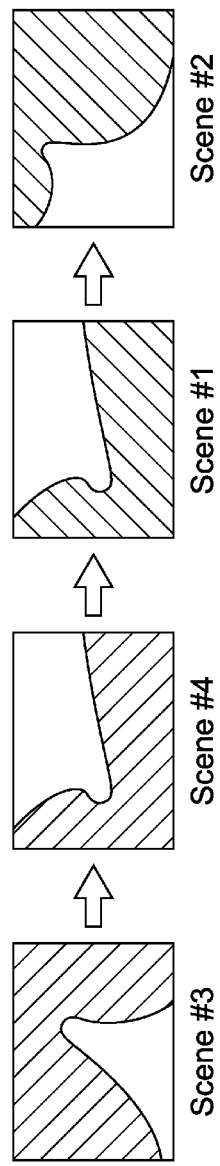
FIG. 14 is a diagram showing an example in which the scene number and the annotation names are added to the scene setting table.
FIG. 15 shows an example of screen transition based on the basic scene setting table.

FIG. 14 is a diagram showing an example in which the scene number and the annotation names are added to the scene setting table. FIG. 14 is obtained by changing the basic scene setting table FIG. 10 as follows. The scene #4 (display order 2) is displayed. After that, a user instructs to switch the displayed scene to the next scene. Then, an annotation "a" and an annotation "b" are displayed on the displayed scene #4.

Figure 16:
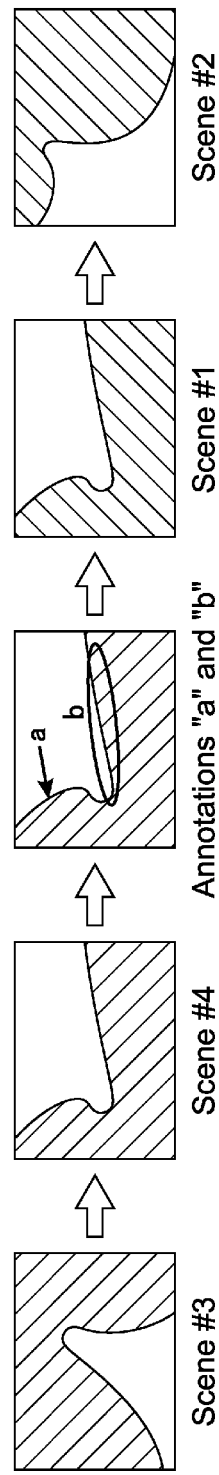
FIG. 16 is a diagram showing an example of screen transition based on the scene setting table of a modified example 3, to which the annotation display behavior is added.

FIG. 15 shows an example of screen transition based on the basic scene setting table of FIG. 10. Further, FIG. 16 shows an example of screen transition based on the scene setting table of the modified example 3, to which the annotation display behavior is added. In the example of FIG. 16, the scene #4 is displayed. After that, a user instructs to switch the scene #4 to the next scene. Then, the annotation "a" (arrow) and the annotation "b" (ellipse) are displayed on the displayed scene #4. Then, the user instructs to switch the displayed scene to the next scene again. Then, the displayed scene is switched to the scene #1.

(Configuration of Digital Pathological Viewer 500)

Next, the hardware configuration of the digital pathological viewer 500 will be described.

Figure 17:
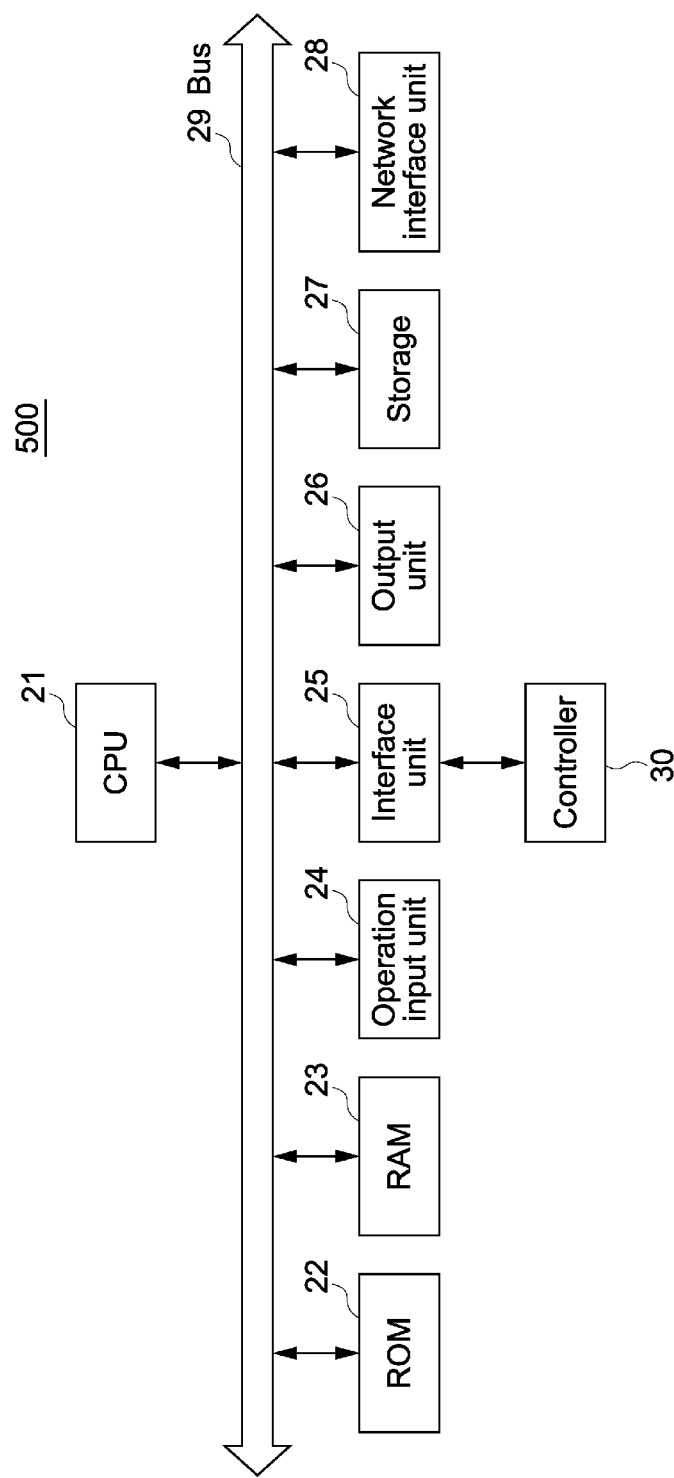
FIG. 17 is a block diagram showing the hardware configuration of the digital pathological viewer 500 of the present technology.

FIG. 17 is a block diagram showing the hardware configuration of the digital pathological viewer 500 of the present technology.

The digital pathological viewer 500 includes a CPU (Central Processing Unit) 21, a ROM (Read Only Memory) 22, a RAM (Random Access Memory) 23, and an operation input unit 24 (input unit). The CPU 21 performs arithmetic control. The RAM 23 is a work memory for the CPU 21. Instructions depending on operation by a user are input in the operation input unit 24. The digital pathological viewer 500 further includes an interface unit 25, an output unit 26 (display unit), storage 27 (storage), a network interface unit 28, and a bus 29 connecting them.

Programs for executing various processes are stored in the ROM 22. A controller 30 is connected to the interface unit 25. The controller 30 includes various buttons and sticks. The controller 30 is configured to receive various kinds of input from a user.

Further, the controller 30 includes a built-in acceleration sensor and a built-in inclination sensor. A user inclines or shakes the controller 30 to thereby input instructions. The controller 30 is configured to receive the instructions to the controller 30 by the user.

The network 300 is connected to the network interface unit 28. The output unit 26 is an image display apparatus such as a liquid crystal display, an EL (Electro Luminescence) display, or a plasma display. The storage 27 is a magnetic disk such as an HDD (Hard Disk Drive), a semiconductor memory, an optical disk, or the like.

The CPU 21 expands a program corresponding to an instruction from the operation input unit 24, out of a plurality of programs stored in the ROM 22, the storage 27, and the like, in the RAM 23. The CPU 21 arbitrarily controls the output unit 26 and the storage 27 based on the expanded program.

The CPU 21 implements functional blocks (described later). The CPU 21 executes the programs stored in the ROM 22, the storage 27, and the like. The CPU 21 as necessary controls the above-mentioned units. Because of this, the digital pathological viewer 500 is capable of implementing the various functional blocks. The digital pathological viewer 500 is capable of causing the respective unit to function as the digital pathological viewer 500.

(Configuration of Digital Pathological Server 400)

Next, the hardware configuration of the digital pathological server 400 will be described.

The hardware configuration of the digital pathological server 400 is basically the same as the hardware configuration of the digital pathological viewer 500 except that the controller 30 is not connected to the interface unit 25. In view of this, detailed description of the hardware configuration of the digital pathological server 400 is omitted (Functional Blocks of Digital Pathological Server 400)

Next, the functional blocks of the digital pathological server 400 will be described. The first main function of the digital pathological server 400 is to provide a pathological image in response to a request from the digital pathological viewer 500.

Figure 18:
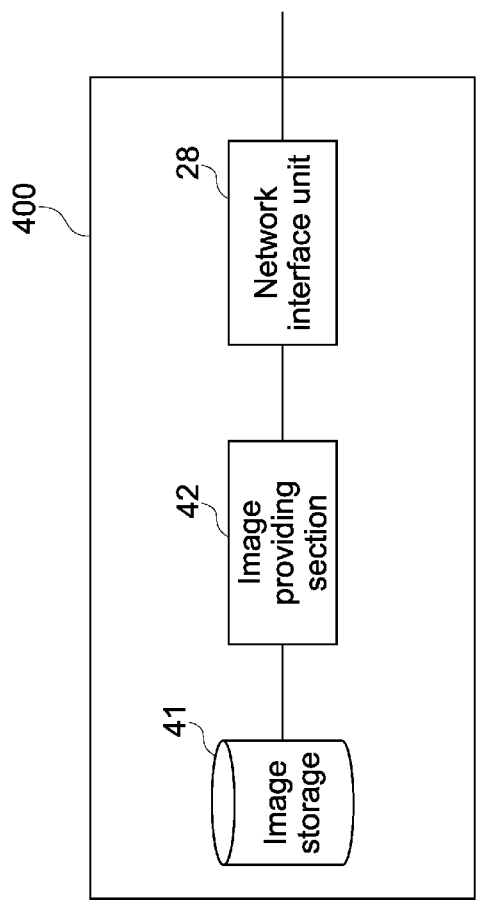
FIG. 18 is a diagram showing the functional blocks of a digital pathological server 400.

The second main function of the digital pathological server 400 is to store comment (hereinafter, referred to as annotation), which a pathologist adds to a particular place of a pathological image by using the viewer. FIG. 18 is a diagram showing the functional blocks of the digital pathological server 400.

The digital pathological server 400 includes the following functional blocks, i.e., image storage 41 and an image providing section 42.

The image storage 41 stores pathological images. The pathological image is divided into tiles, and JPEG compressed. The image providing section 42 provides the stored pathological images to the digital pathological viewer 500 in response to a request from the digital pathological viewer 500. Further, the image storage 41 also stores annotation, which a user adds to a pathological image by using the viewer of the digital pathological viewer 500.

The digital pathological viewer 500 sends an image request via the network 300. The image providing section 42 obtains pathological images, which correspond to the image request, from the image storage 41. The image providing section 42 sends the pathological images to the digital pathological viewer 500 via the network 300.

Note that the digital pathological server 400 and the digital pathological viewer 500 configure a client-server system. In this situation, functions that the client has and functions that the server has may be determined as necessary. In view of this, the digital pathological server 400 does not necessarily execute the above-mentioned functional blocks. Alternatively, the digital pathological viewer 500 as a client may execute the above-mentioned functional blocks.

(Functional Blocks of Digital Pathological Viewer 500)

Next, the functional blocks of the digital pathological viewer 500 will be described. The first main function of the digital pathological viewer 500 is to receive operational instructions from a pathologist as a user, to obtain an appropriate pathological image from the digital pathological server 400, and to display the pathological image to a user.

The second main function of the digital pathological viewer 500 is to store information on displayed images, which are specified as scenes by a user, and to store the order and setting for reproducing a plurality of scenes based on the framework of presentation. The third main function of the digital pathological viewer 500 is to reproduce scenes based on the stored order and the stored setting during presentation.

Figure 19:
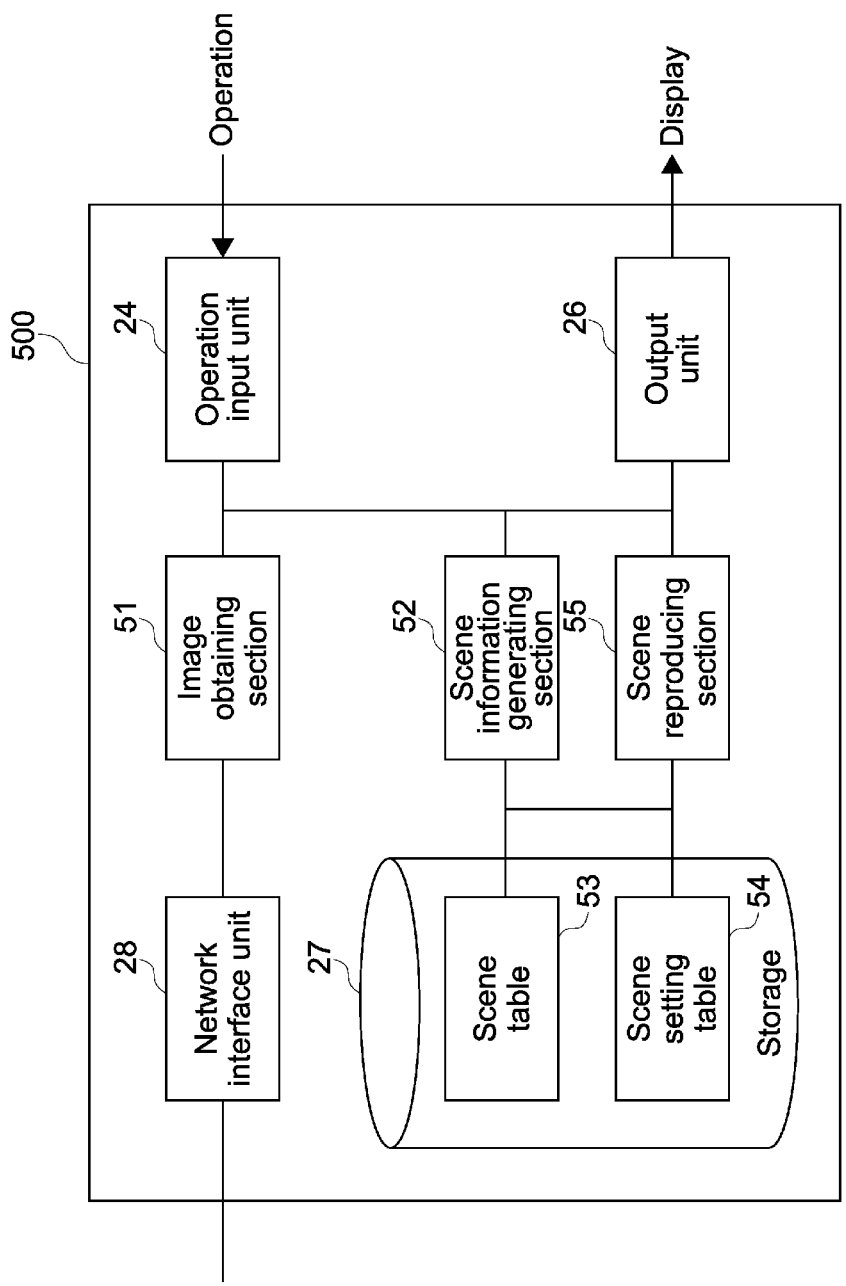
FIG. 19 is a diagram showing the functional blocks of the digital pathological viewer 500.

FIG. 19 is a diagram showing the functional blocks of the digital pathological viewer 500.

The digital pathological viewer 500 includes the following functional blocks, i.e., an image obtaining section 51 (obtaining section, display processing section), a scene information generating section 52 (generating section), a scene table 53, a scene setting table 54, and a scene reproducing section 55 (reproducing section).

The operation input unit 24 receives an instruction from a pathologist as a user, and inputs the instruction in the image obtaining section 51. The image obtaining section 51 obtains a pathological image, which corresponds to the instruction, from the digital pathological server 400 via the network 300. The image obtaining section 51 presents the obtained pathological image to the user by using the output unit 26.

The scene information generating section 52 stores the coordinate and the display magnification of the presented image in the scene table 53 as scene information in response to an instruction, which is input by a user when the pathological image is presented to the user. Further, the scene information generating section 52 receives, for example, the order of reproducing scenes stored in the scene table 53 from a user via the operation input unit 24. The scene information generating section 52 stores the order in the scene setting table 54.

The scene table 53 receives scene information of each scene from the scene information generating section 52. The scene table 53 stores the scene information. The scene reproducing section 55 uses the scene information, which is stored in the scene table 53, to reproduce each scene during presentation.

The scene setting table 54 stores information such as the order, which is used when the scene reproducing section 55 reproduces the respective scenes. A user sets information such as order by using the scene information generating section 52. The scene reproducing section 55 uses information such as order, which is stored in the scene setting table 54, to determine the presentation order of scenes during presentation.

The scene reproducing section 55 reproduces each scene based on scene information in the scene table 53 when a user makes a presentation. Further, the scene reproducing section 55 determines the order of reproducing scenes, a method of switching a scene to another scene, and the like, based on information in the scene setting table 54.

The functional blocks of the digital pathological viewer 500 have been described above. Note that the digital pathological viewer 500 and the digital pathological server 400 configure a client-server system. In this situation, functions of the client and functions of the server may be determined as necessary. In view of this, the digital pathological viewer 500 does not necessarily execute the above-mentioned functional blocks. Alternatively, the digital pathological server 400 as a server may execute the above-mentioned functional blocks.

(Prefetch (No. 1))

Next, how to prefetch tiles in a cache will be described. As described above, digital pathological slide data is image data, which has an extremely large volume. Because of this, in general, the digital pathological slide data is divided into tiles, image compression such as JPEG is performed for each tile, and the tiles are stored in the digital pathological server 400.

Figure 20:
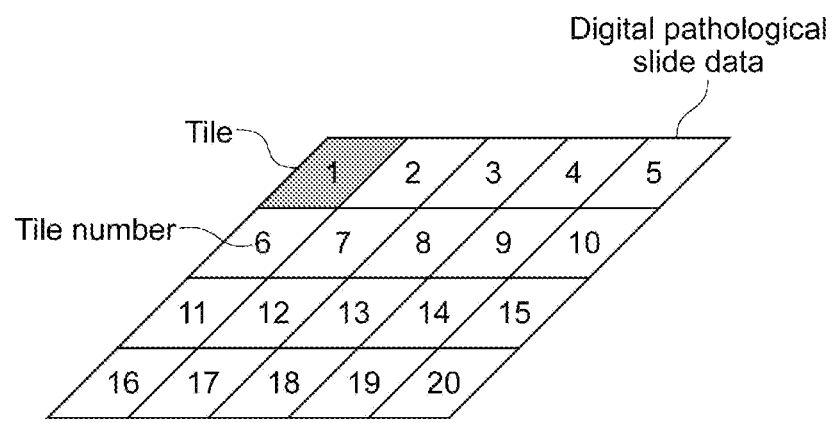
FIG. 20 is a diagram showing an example in which digital pathological slide data is divided into tiles.

FIG. 20 is a diagram showing an example in which digital pathological slide data is divided into tiles. In this example a digital pathological slide is divided into 5×4 tiles.

Figure 21:
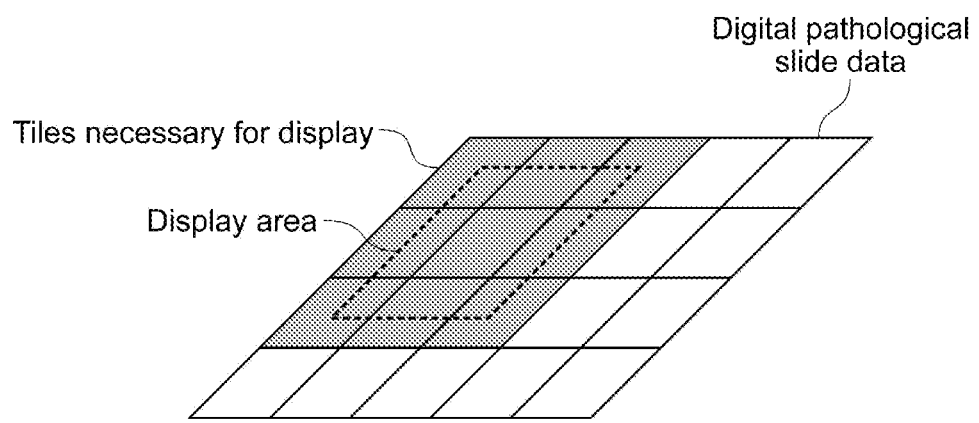
FIG. 21 is a diagram showing the relation between an area, which is displayed on the screen of the digital pathological viewer 500, and the necessary tiles.

Next, FIG. 21 shows the relation between an area, which is displayed on the screen of the digital pathological viewer 500, and the necessary tiles. In this example, the digital pathological viewer 500 displays the display area of FIG. 21. In this case, the image is displayed by using the nine tiles having the tile numbers 1, 2, 3, 6, 7, 8, 11, 12, and 13.

If a scene is decided, the necessary tiles are decided. Because of this, when a user makes a presentation, it is possible to previously obtain (prefetch) tiles necessary to display the next scene from the digital pathological server 400, and to store in a cache.

Figure 22:
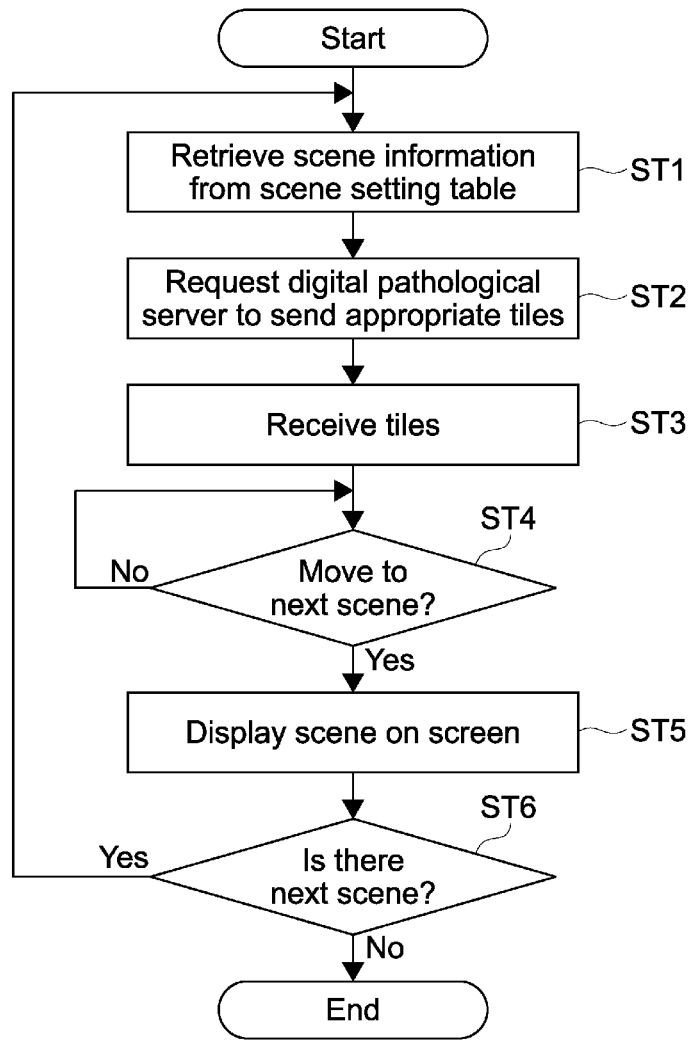
FIG. 22 is a flowchart showing the flow of the process of prefetching tiles necessary to display a scene based on scene information.

FIG. 22 is a flowchart showing the flow of the process of prefetching tiles necessary to display a scene based on scene information.

First, the scene reproducing section 55 determines the scene number of a scene, which will be displayed next, from the scene setting table 54. The scene reproducing section 55 retrieves appropriate scene information (Step ST1).

As described above, if a scene is determined, the tile numbers of tiles to be retrieved are determined. The scene reproducing section 55 requests the digital pathological server 400 to send appropriate tiles by means of the image obtaining section 51 (Step ST2).

The scene reproducing section 55 receives the appropriate tiles (Step ST3). Then, the scene reproducing section 55 waits for an instruction to switch to the next scene (Step ST4). A user operates a mouse or the controller 30 to thereby input the instruction.

The scene reproducing section 55 receives the instruction to switch to the next scene (Step ST4, Yes). Then, the scene reproducing section 55 displays the next scene on the screen of the digital pathological viewer 500 (Step ST5). Further, the scene reproducing section 55 checks if there is a next scene to be displayed (Step ST6).

If there is a next scene to be displayed (Step ST6, Yes), the scene reproducing section 55 returns to Step ST1. The scene reproducing section 55 obtains tiles based on the scene information.

Note that, if the RAM 23 of the digital pathological viewer 500 has the necessary volume, all the tiles necessary for all the scenes may be previously obtained collectively.

The flow of the process of prefetching tiles has been described. By prefetching tiles, the digital pathological viewer 500 is capable of displaying scenes on the screen at high speed.

(Prefetch (No. 2))

Figure 23:
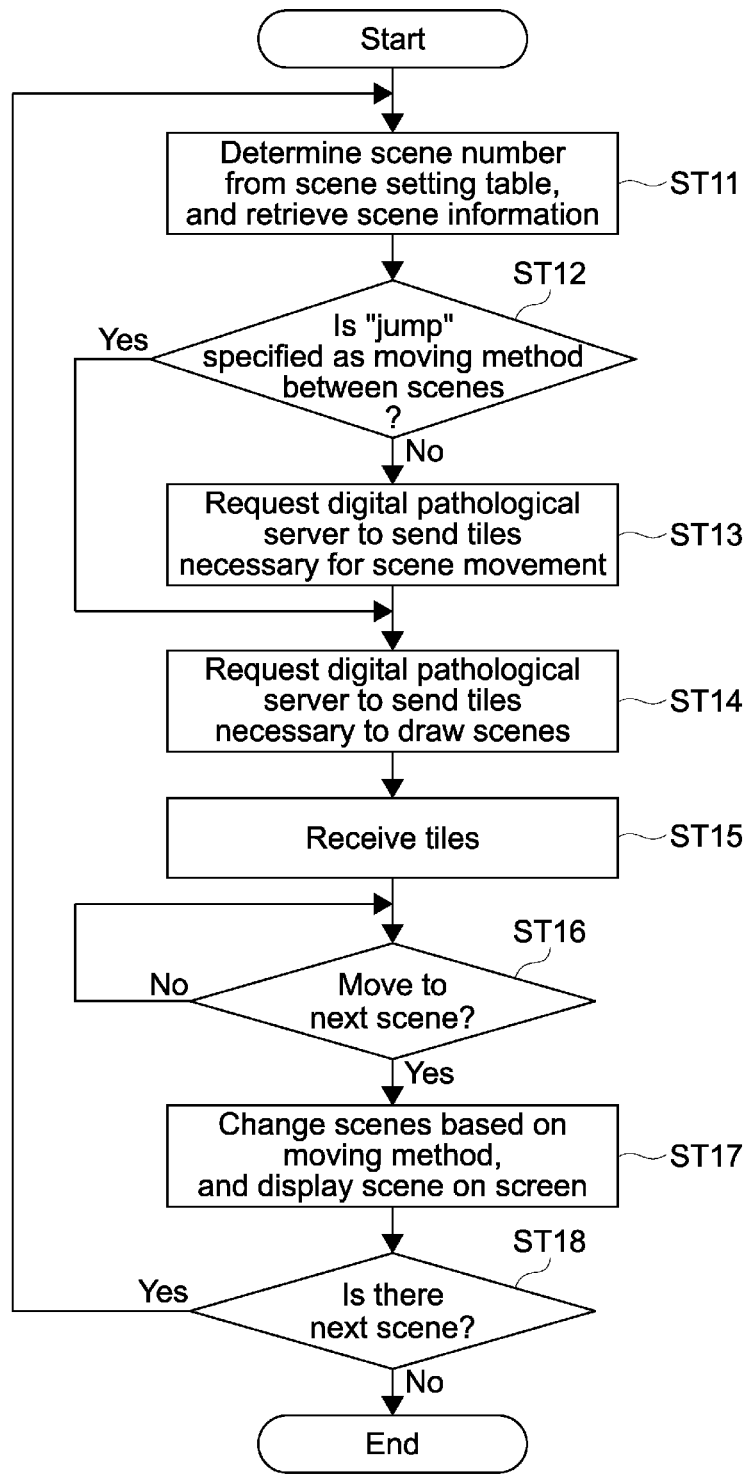
FIG. 23 is a flowchart showing the flow of the process of prefetching tiles, which are necessary to display scenes and to display movement from a scene to another scene, based on scene information.

To previously obtain tiles is effective not only in displaying scenes at high speed, but also in displaying movement from a scene to another scene at high speed. FIG. 23 is a flowchart showing the flow of the process of prefetching tiles, which are necessary to display scenes and to display movement from a scene to another scene, based on scene information.

First, the scene reproducing section 55 determines the scene number of a scene, which will be displayed next, from the scene setting table 54. The scene reproducing section 55 retrieves appropriate scene information (Step ST11).

If "jump" is specified as a moving method between scenes (Step ST12, Yes), nothing is drawn during movement.

If "animation" or "zoom out and zoom in" is specified as a moving method between scenes (Step ST12, No), the scene reproducing section 55 requests the digital pathological server 400 to send tiles, which are necessary to draw an image during movement display, by means of the image obtaining section 51 (Step ST13).

Next, the scene reproducing section 55 requests the digital pathological server 400 to send tiles, which are necessary to draw the scenes (Step ST14).

The scene reproducing section 55 receives the tiles (Step ST15). Then, the scene reproducing section 55 waits for an instruction to switch to the next scene (Step ST16). A user operates a mouse or the controller 30 to thereby input the instruction.

The scene reproducing section 55 receives the instruction to switch to the next scene (Step ST16, Yes). Then, the scene reproducing section 55 displays movement on the screen based on the specified moving method (Step ST17). Further, the scene reproducing section 55 checks if there is a next scene to be displayed with reference to the scene setting table 54 (Step ST18).

If there is a next scene to be displayed (Step ST18, Yes), the scene reproducing section 55 returns to Step ST11. The scene reproducing section 55 obtains tiles based on the scene information.

Note that, the image displayed on the screen during movement is not used for diagnosis. So the image quality may be low. In view of this, an image may not be drawn at fourtyfold magnification. Instead, tiles of an image at twentyfold magnification may be enlarged twice in the vertical and horizontal directions (area ratio: fourfold), and movement may be displayed. The magnification of tiles, which are used for movement display, is set in this manner. As a result, it is possible to reduce the data amount of tiles, which are necessary to draw movement to and from scenes, and the data amount may be quarter.

(How to Switch Display/Non-Display of Menu, Etc.)

Next, how to switch display/non-display of menu and the like on the screen of the digital pathological viewer 500 will be described.

Figure 24:
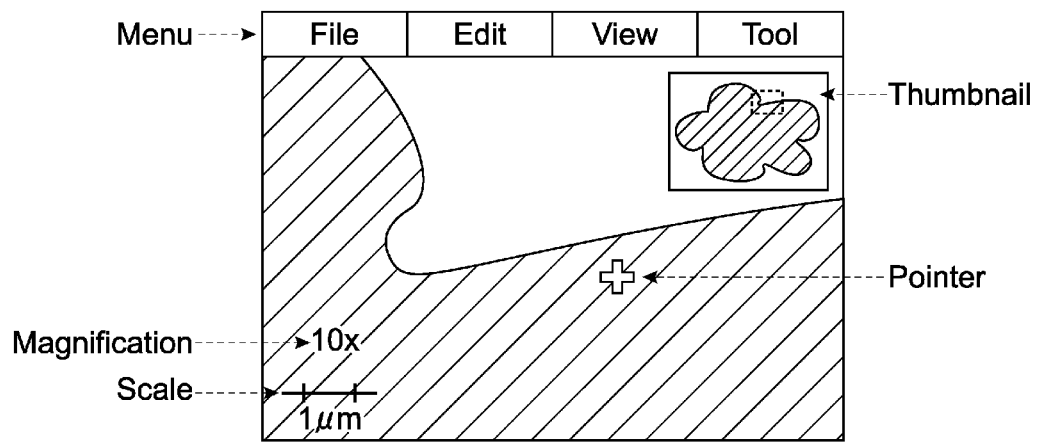
FIG. 24 is a diagram showing an example of the screen layout of the digital pathological viewer 500 in a case of making a usual diagnosis by using an image.

First, FIG. 24 shows an example of the screen layout of the digital pathological viewer 500 in a case of making a usual diagnosis by using an image. It is assumed that the digital pathological viewer 500 will be used for image diagnosis. So the digital pathological viewer 500 includes a menu for selecting a file, for adding note (annotation) about diagnosis, for rotating an image, for adjusting colors of an image, and for setting various conditions.

Further, it is necessary to display a thumbnail, a pointer, magnification, a scale, and the like, in addition to the menu. The thumbnail shows which area in the entire digital pathological slide is displayed. The pointer shows the operation target position. The magnification display shows the magnification (enlargement factor) with respect to the pixel same magnification. The scale display shows how many micrometers a scale mark indicates.

However, all the functions are not necessarily used during presentation. Scene information of scenes is previously registered in the scene table 53, and the scenes are switched and displayed. Because of this, operations such as file selection, coordinate position adjustment, magnification adjustment, color adjustment, annotation addition, and the like are not necessary. In view of this, the scene reproducing section 55 may not display the menu and the pointer.

Figure 25:
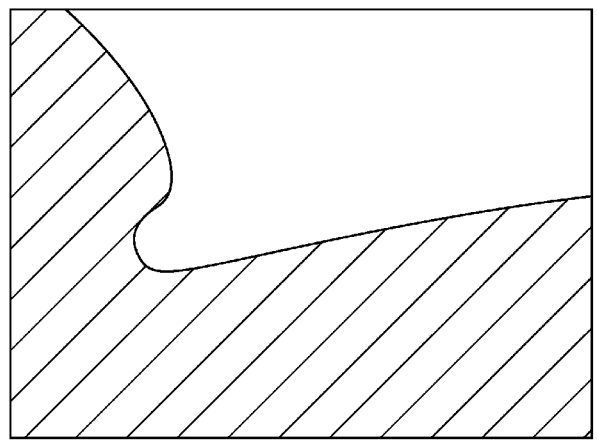
FIG. 25 is a diagram showing an example in which a menu, a pointer, a thumbnail, magnification, a scale, and the like are not displayed on the screen layout example of FIG. 24.

Further, if the thumbnail, the magnification, the scale, and the like are not displayed, the scene reproducing section 55 may display an image on the screen as if a user looks through an optical microscope. FIG. 25 is a diagram showing an example in which a menu, a pointer, a thumbnail, magnification, a scale, and the like are not displayed on the screen layout example of FIG. 24.

(Other Configuration of Present Technology)

(1)

An information processing apparatus comprising a processor; and a memory device storing instructions which when executed by the processor, causes the processor to generate scene information to reproduce display of at least one selected area of a pathological image; and receive order information corresponding to the scene information based on a user input.

(2)

The information processing apparatus according to (1), wherein the scene information includes position information, magnification information, and rotation angle information.

(3)

The information processing apparatus according to any one of (1) and (2), wherein the instructions further cause the processor to generate moving information indicating a method of moving between a first selected area of the pathological image and a second selected area of the pathological image.

(4)

The information processing apparatus according to (3), wherein the method of moving includes at least of one an animation, a jump, a zoom in, and a zoom out.

(5)

The information processing apparatus according to any one of (1) to (4), wherein the instructions further cause the processor to generate display time information indicating a time period for displaying the at least one selected area of the pathological image.

(6)

The information processing apparatus according to any one of (1) to (5), wherein the instructions further cause the processor to generate annotation information indicating annotations to be displayed with the at least one selected area of the pathological image.

(7)

The information processing apparatus according to any one of (1) to (6), wherein the instructions further cause the processor to control display of the at least one selected area of the pathological image.

(8)

The information processing apparatus according to any one of (1) to (7), wherein the scene information includes depth information of the at least one selected area of the pathological image.

(9)

The information processing apparatus according to any one of (1) to (8), wherein the scene information is generated based on an image displayed on a display screen.

(10)
An information processing method comprising generating scene information to reproduce display of at least one selected area of a pathological image; and receiving order information corresponding to the scene information based on a user input.

(11)
A non-transitory computer readable storage medium storing a computer program for causing an apparatus to generate scene information to reproduce display of at least one selected area of a pathological image; and receive order information corresponding to the scene information based on a user input.

(12)
An information processing system comprising: a processor; and a memory device storing instructions which when executed by the processor, causes the processor to: generate scene information to reproduce display of at least one selected area of a pathological image; and receive order information corresponding to the scene information based on a user input.

(13)
The information processing system according to (12), further comprising a server configured to store the pathological image.

(14)
The information processing system according to any one of (12) and (13), further comprising a pathological scanner configured to capture the pathological image.

(15)
An information processing apparatus comprising: a generating unit configured to generate scene information to reproduce display of at least one selected area of a pathological image; and a receiving unit configured to receive order information corresponding to the scene information based on a user input.

(16)
An information processing apparatus comprising: a processor; and a memory device storing instructions which when executed by the processor, causes the processor to: receive scene information to display at least one selected area of a pathological image and order information corresponding to an order of the scene information; and control display of the at least one selected area of the pathological image in the order based on the scene information and the order information.

(17)
The information processing apparatus according to (16), wherein the instructions further cause the processor to switch between display and non-display of display elements displayed with the at least one selected area of the pathological image.

(18)
The information processing apparatus according to any one of (16) and (17), wherein the scene information is received based on an image displayed on a display screen.

(19)
An information processing method comprising: receiving scene information to display at least one selected area of a pathological image and order information corresponding to an order of the scene information; and controlling display of the at least one selected area of the pathological image in the order based on the scene information and the order information.

(20)
A non-transitory computer readable storage medium storing a computer program for causing an apparatus to: receive scene information to display at least one selected area of a pathological image and order information corresponding to an order of the scene information; and control display of the at least one selected area of the pathological image in the order based on the scene information and the order information.

(21)
An information processing system comprising: a processor; and a memory device storing instructions which when executed by the processor, causes the processor to: receive scene information to display at least one selected area of a pathological image and order information corresponding to an order of the scene information; and control display of the at least one selected area of the pathological image in the order based on the scene information and the order information.

(22)
The information processing system according to (21), further comprising a server configured to store the pathological image.

(23)
The information processing system according to any one of (21) and (22), further comprising a pathological scanner configured to capture the pathological image.

(24)
An information processing apparatus comprising: a reception unit configured to receive scene information to display at least one selected area of a pathological image and order information corresponding to an order of the scene information; and a display control unit configured to control display of the at least one selected area of the pathological image in the order based on the scene information and the order information.

(25)
An information processing system comprising: at least one processor; and a memory device storing instructions which when executed by the at least one processor, causes the processor to: generate scene information to reproduce display of at least one selected area of a pathological image; receive order information corresponding to the scene information based on a user input; and control display of the at least one selected area of the pathological image in the order based on the scene information and the order information.

(26)
The information processing system according to (25), further comprising a server configured to store the pathological image.

(27)
The information processing system according to any one of (25) and (26), further comprising a pathological scanner configured to capture the pathological image.

(28)
An information processing apparatus, comprising:
  a display processing section configured
    to receive selection of an area of a pathological image in an entire pathological image from a user, the area being to be displayed, and
    to cause a display unit to display the pathological image of the selected area;
  a generating section configured
    to receive selection of at least one pathological image out of a plurality of sequentially-displayed pathological images, from the user, and
    to generate information necessary to display the selected pathological images, as scene information;
  an input unit configured to receive setting of order information on the at least one scene information, from the user;

storage configured to store the at least one generated scene information and the set order information; and a reproducing section configured to cause the display unit to sequentially display the at least one pathological image selected by the user based on the stored information.

(29) The information processing apparatus according to (28), further comprising:

an obtaining section configured to obtain a pathological image of the selected area from an image storing apparatus, the image storing apparatus storing the entire pathological image.

(30) The information processing apparatus according to (28) or (29), wherein the reproducing section is configured to receive information on how to change display when switching the sequentially-displayed pathological images, from the user, and when the at least one pathological image selected by the user is sequentially displayed on the display unit, to switch display of the plurality of pathological images based on the information on how to change display.

(31) The information processing apparatus according to (30), wherein the reproducing section is configured, when switching display of the plurality of sequentially-displayed pathological images, to display at least one image spatially existing between the images before and after switching such that the at least one image moves between the pathological images before and after switching.

(32) The information processing apparatus according to (30), wherein the reproducing section is configured, when switching display of the plurality of sequentially-displayed pathological images, to temporarily zoom out an image before switching and to display the image, and to zoom in an image after switching and to display the image.

(33) The information processing apparatus according to (30), wherein the information on how to change display further includes display time period information of a corresponding pathological image, and the reproducing section is configured to switch the display based on the display time period information.

(34) The information processing apparatus according to (29), wherein the reproducing section is configured to cause the obtaining section to collectively obtain pathological images of the selected areas based on the stored scene information, before the display unit displays the at least one pathological image.

(35) The information processing apparatus according to any one of (28) to (34), wherein the reproducing section is capable of switching turning on/off of display of a display element based on an instruction from the user, when the display unit sequentially displays the at least one pathological image selected by the user, the display element being used when a user observes a pathological image.

(36) An information processing method, comprising:

receiving, by a display processing section, selection of an area of a pathological image in an entire pathological image from a user, the area being to be displayed;

causing, by the display processing section, a display unit to display the pathological image of the selected area;

receiving, by a generating section, selection of at least one pathological image out of a plurality of sequentially-displayed pathological images, from the user;

generating, by the generating section, information necessary to display the selected pathological images, as scene information;

receiving, by an input unit, setting of order information on the at least one scene information, from the user;

storing, by storage, the at least one generated scene information and the set order information; and causing, by a reproducing section, the display unit to sequentially display the at least one pathological image selected by the user based on the stored information.

(37) An information processing program, causing a computer to function as:

a display processing section configured to receive selection of an area of a pathological image in an entire pathological image from a user, the area being to be displayed, and to cause a display unit to display the pathological image of the selected area;

a generating section configured to receive selection of at least one pathological image out of a plurality of sequentially-displayed pathological images, from the user, and to generate information necessary to display the selected pathological images, as scene information;

an input unit configured to receive setting of order information on the at least one scene information, from the user;

storage configured to store the at least one generated scene information and the set order information; and a reproducing section configured to cause the display unit to sequentially display the at least one pathological image selected by the user based on the stored information.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 10 microscope
20 scanner computer
21 CPU
22 ROM
23 RAM
24 operation input unit
25 interface unit
26 output unit
27 storage
28 network interface unit
29 bus
41 image storage
42 image providing section
51 image obtaining section 52 scene information generating section
53 scene table
54 scene setting table
55 scene reproducing section
100 digital pathological scanner
300 network
400 digital pathological server
500 digital pathological viewer

The invention claimed is:

1. An information processing apparatus comprising:
a processor; and a memory device storing instructions which when executed by the processor, causes the processor to: cause a display device to display a first area of a pathological image; receive a position information of a second area of the pathological image; and
cause the display device to gradually move a display area from the first area to a third area that includes the first area and the position information of the second area, such that a positional relationship between the first area and the second area of the pathological image is displayed, wherein gradually moving the position of the display area includes zooming out from the first area of the pathological image to the third area to provide an understanding of a position of the display area within the whole pathological image before zooming in to the second area of the pathological image.

2. The information processing apparatus according to claim 1, wherein the instructions further cause the processor to:
generate scene information including position information, magnification information, and rotation angle information.

3. The information processing apparatus according to claim 1, wherein the instructions further cause the processor to:
generate moving information indicating a method of moving between the first area of the pathological image and the second selected area of the pathological image.

4. The information processing apparatus according to claim 3, wherein the method of moving includes at least of one an animation, a jump, a zoom in, and a zoom out.

5. The information processing apparatus according to claim 1, wherein the instructions further cause the processor to:
generate display time information indicating a time period for displaying at least one area of the pathological image.

6. The information processing apparatus according to claim 1, wherein the instructions further cause the processor to:
generate annotation information indicating annotations to be displayed with at least one area of the pathological image.

7. The information processing apparatus according to claim 1, wherein the instructions further cause the processor to:
control display of at least one selected area of the pathological image.

8. The information processing apparatus according to claim 2, wherein the scene information includes depth information of at least one selected area of the pathological image.

9. The information processing apparatus according to claim 2, wherein the scene information is generated based on an image displayed on a display screen.

10. An information processing method comprising:
causing a display device to display a first area of a pathological image;
receiving a position information of a second area of the pathological image; and
causing the display device to gradually move a display area from the first area to a third area that includes the first area and the position information of the second area, such that a positional relationship between the first area and the second area of the pathological image is displayed, wherein gradually moving the position of the display area includes zooming out from the first area of the pathological image to the third area to provide an understanding of a position of the display area within the whole pathological image before zooming in to the second area of the pathological image.

11. A non-transitory computer readable storage medium storing a computer program for causing an apparatus to perform the method of claim 10.

12. An information processing system comprising the information processing apparatus of claim 1.

13. The information processing system according to claim 12, further comprising:
a server configured to store the pathological image.

14. The information processing system according to claim 12, further comprising:
a pathological scanner configured to capture the pathological image.

15. An information processing apparatus comprising:
a processor; and
a memory device storing instructions which when executed by the processor, causes the processor to:
cause a display device to display a first area of a pathological image;
receive a position information of a second area of the pathological image; and
cause the display device to gradually move a display area from the first area to a third area that includes the first area and the position information of the second area, such that a positional relationship between the first area and the second area of the pathological image is displayed, wherein gradually moving the position of the display area includes zooming out from the first area of the pathological image to the third area provide an understanding of a position of the display area within the whole pathological image before zooming in to the second area of the pathological image.

16. The information processing apparatus according to claim 15, wherein the instructions further cause the processor to:
switch between display and non-display of display elements displayed with at least one selected area of the pathological image.

17. The information processing apparatus according to claim 15, wherein scene information is received based on an image displayed on a display screen.

18. An information processing system comprising the information processing apparatus of claim 15.

19. The information processing system according to claim 18, further comprising:
a server configured to store the pathological image.

20. The information processing system according to claim 18, further comprising:
a pathological scanner configured to capture the pathological image.

* * * * *